US012758198B2

(12) United States Patent
Chen

(10) Patent No.: US 12,758,198 B2
(45) Date of Patent: Oct. 13, 2026

(54) ROTARY AND TELESCOPIC SPERM EXTRACTOR

(71) Applicant: Zhejiang lianhong Technology Co., LTD, Huzhou (CN)

(72) Inventor: Xiu Chen, Hangzhou (CN)

(73) Assignee: ZhejianglianhongTechnology Co., LTD, Zhejiang (CN)

( * ) Notice: Subject to any disclaimer, the term of this patent is extended or adjusted under 35 U.S.C. 154(b) by 431 days.

(21) Appl. No.: 18/513,962

(22) Filed: Nov. 20, 2023

(65) Prior Publication Data

US 2024/0415498 A1 Dec. 19, 2024

(30) Foreign Application Priority Data

Jun. 19, 2023 (CN) ........................ 202310735991.7

(51) Int. Cl.
*A61B 10/00* (2006.01)
*A61H 19/00* (2006.01)

(52) U.S. Cl.
CPC ......... *A61B 10/0058* (2013.01); *A61H 19/32* (2013.01)

(58) Field of Classification Search
CPC .... A61B 10/0058; A61B 90/98; A61H 19/32; Y02A 40/81; H02K 7/075; H02K 7/116; H02K 7/14; H02K 13/003
See application file for complete search history.

(56) References Cited

U.S. PATENT DOCUMENTS

| | | | | |
|---|---|---|---|---|
| 2020/0046599 A1* | 2/2020 | Sedic | ........................ | A61F 5/41 |
| 2021/0186798 A1* | 6/2021 | Tang | ...................... | A61H 19/32 |

FOREIGN PATENT DOCUMENTS

| | | | |
|---|---|---|---|
| CN | 212729939 U | 3/2021 | |
| CN | 215536407 U | 1/2022 | |
| CN | 217285852 U | 8/2022 | |
| CN | 116270186 A * | 6/2023 | ............ A61H 19/30 |

* cited by examiner

*Primary Examiner* — Alex M Valvis
*Assistant Examiner* — Jonathan M Haney
(74) *Attorney, Agent, or Firm* — Nitin Kaushik

(57) ABSTRACT

A novel rotary and telescopic sperm extractor is disclosed. The sperm extractor includes a telescopic mechanism; a rotary mechanism mounted on the telescopic mechanism; and an inner container mounted on the rotary mechanism, where the rotary mechanism rotates while making a reciprocating telescopic motion along with the telescopic mechanism. The rotary mechanism includes a second motor which drives a second gear that has a hollow structure. A rotary conductive slip ring is arranged within the hollow structure to stably transmit electrical power during continuous rotation of the gear. The inner container is replaceable, and its tail end is provided with a circuit board equipped with metal contacts. This circuit board interfaces with elastic metal columns on the rotating component to achieve power supply and identification. This design addresses the technical challenge of providing stable power and data communication to a replaceable inner container undergoing simultaneous rotary and telescopic motion.

8 Claims, 7 Drawing Sheets

ROTARY AND TELESCOPIC SPERM EXTRACTOR

CROSS-REFERENCE TO RELATED APPLICATIONS

The application claims priority to Chinese patent application No. 2023107359917, filed on Jun. 19, 2023, the entire contents of which are incorporated herein by reference.

TECHNICAL FIELD

The present invention relates to the technical field of sperm extraction devices, and specifically to a novel rotary and telescopic sperm extractor.

BACKGROUND

With the continuous development of economy and society, people's life pressure is also increasing, leading to declined male sperm motility and increasingly prominent infertility. During doctor seeing in existing hospitals, it is often required to extract sperms within a short time and perform various tests on seminal fluids.

However, an existing medical sperm extractor, such as a sperm extractor provided in Chinese patent CN202222113636.X, is incapable of being freely telescopic or rotatable due to being fixed, has poor sperm extraction, and may bring discomfort to patient's bodies. Therefore, a new device needs to be provided to solve the above problems.

SUMMARY

In view of the problems in the prior art, the present invention provides a novel rotary and telescopic sperm extractor.

To achieve the above objective, the present invention adopts the following specific solution:

The present invention provides a novel rotary and telescopic sperm extractor, including:

a telescopic mechanism;

a rotary mechanism mounted on the telescopic mechanism; and an inner container mounted on the rotary mechanism, where the rotary mechanism rotates while making a reciprocating telescopic motion along with the telescopic mechanism, the telescopic mechanism includes a first motor, an eccentric wheel, and a rocker bar, the eccentric wheel is mounted on the first motor, the rocker bar has one end arranged on the eccentric wheel and the other end mounted on the rotary mechanism, the first motor drives the eccentric wheel to rotate, the eccentric wheel rotates to drive the rocker bar to make a push-pull motion so as to implement the reciprocating telescopic motion of the rotary mechanism, and the inner container makes a reciprocating telescopic and rotary motion along with the rotary mechanism.

Further, the telescopic mechanism further includes slide rods and a slide block:

a slide rod is arranged on each of two sides of the slide block, one end, away from the first motor, of the rocker bar is mounted on the slide block, the slide block is pushed and pulled to make a reciprocating motion on the two slide rods, and the rotary mechanism is mounted on the slide block.

Further, the rotary mechanism includes a second motor:

the second motor is mounted on the slide block and rotates by a rotary shaft;

a first gear is further mounted on the rotary shaft of the second motor; the first gear is further connected to a second gear in a meshed manner; and a hollow structure is further arranged inside the second gear, and a rotary conductive slip ring is arranged in the hollow structure and configured to conduct electricity during rotation of the second gear.

Further, a disc plate is further arranged on the second gear and rotates along with the second gear:

three elastic metal columns are further mounted on the disc plate;

a rotary barrel is further mounted on the disc plate;

a first slip ring is further arranged on an outer side of a front end of the rotary barrel; and a second slip ring is further arranged on a right side of the first slip ring and further sleeved with a third slip ring, and the third slip ring is mounted on a shell.

Further, the inner container includes a soft rubber channel located in the rotary barrel, and a butt joint assembly is further mounted at a tail end of the soft rubber channel;

the butt joint assembly includes a first bracket, a circuit board, and a first housing;

the first bracket is embedded into the tail end of the soft rubber channel, the circuit board is mounted on the first bracket, and the first housing is located on an outer side of the circuit board and mounted at the tail end of the soft rubber channel: and three metal contacts are arranged on the circuit board and extend to an outer side of the first housing to be in butt joint with the elastic metal columns.

Further, the circuit board is further provided with an identification chip configured to store identification information of the inner container so as to cause the sperm extractor to activate a corresponding mode.

Further, an opening is further formed in a front end of the soft rubber channel, and a barbed member is further arranged at the opening and configured to prevent internal liquid from flowing out.

Further, a second bracket is further arranged at the front end of the soft rubber channel and embedded into the soft rubber channel;

a fixing ring is further mounted on an outer side of the second bracket;

a clamping strip is further arranged on an outer wall of the second bracket; a clamping groove is correspondingly formed in an inner wall of the fixing ring, and the clamping strip rotates and then is clamped into the clamping groove to fix the fixing ring to the second bracket;

a positioning strip is further arranged on an outer wall of the fixing ring;

a third bracket is further mounted on the fixing ring;

a plurality of clamping columns are further arranged on one side of the third bracket that faces the fixing ring: and a plurality of mounting holes are correspondingly formed in the fixing ring, and the clamping columns are inserted into the mounting holes to fix the third bracket to the fixing ring.

Further, two first magnets are further arranged in the first housing, and magnetic iron blocks are further arranged at corresponding positions of the disc plate:

a second magnet and a third magnet are further mounted on one side of the second bracket and one side of the first slip ring that are close to each other, respectively; and the first magnets and the magnetic iron blocks attract each other, and the second magnet and the third magnet attract each other for adsorptive positioning.

Further, a soft rubber plug is further arranged at the tail end of the soft rubber channel through the circuit board and the first housing and configured to be taken down during cleaning so as to filter out remaining water inside:

a battery is further arranged in the shell and mounted on a fixing rack, and a button is further arranged on the shell: and a control mainboard is further arranged on the fixing rack and connected to the battery, the first motor, the second motor, the button, and the circuit board.

With the technical solution of the present invention, the following beneficial effects are achieved:

1. The rotary motion can be made during the telescopic motion.
2. The three elastic metal columns on the disc plate are in butt joint with the three metal contacts on the first housing, making it convenient for replacement of different inner containers.
3. The first magnets and the magnetic iron blocks attract each other, and the second magnet and the third magnet attract each other, such that the inner container is in butt joint with the shell accurately by adsorptive positioning.
4. The inner container provided with the identification chip, making it convenient for the sperm extractor body to activate the corresponding mode based on information of the identification chip.
5. The barbed member is arranged at the opening to prevent the internal liquid from flowing out.

Figure 1:
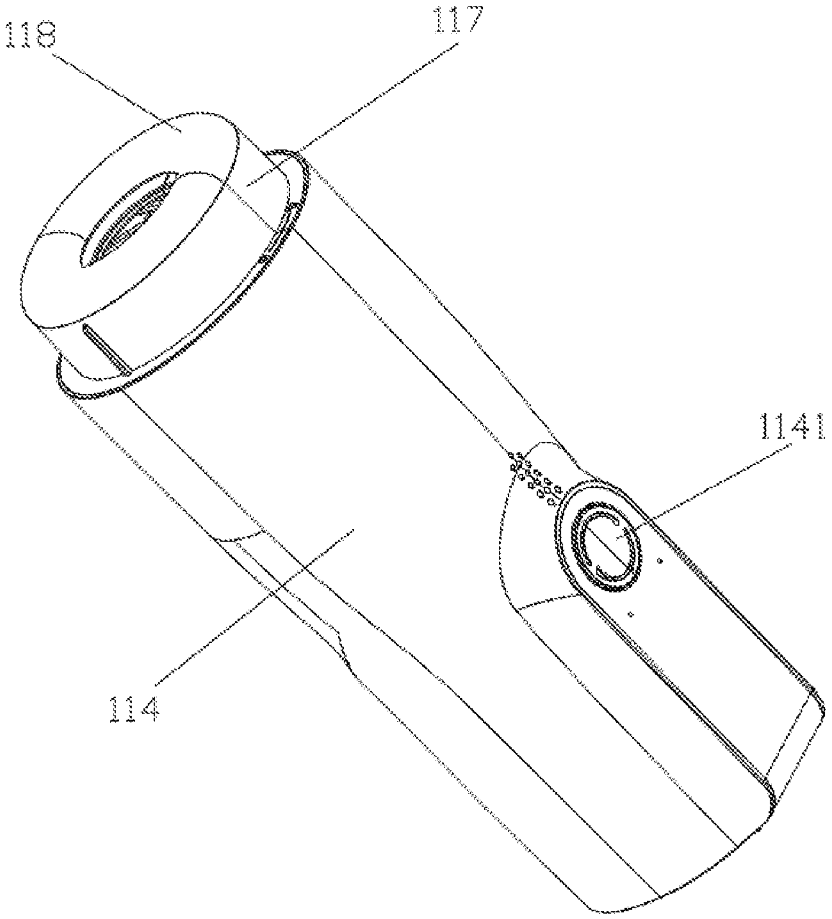
FIG. 1 is a three-dimensional view of the present invention.

101. first motor; 102. eccentric wheel; 103. rocker bar; 104. slide rod; 105. slide block;

106. second motor; 107. first gear; 108. second gear; 1081. rotary conductive slip ring;

109. disc plate; 1091. elastic metal column; 110. rotary barrel;

111. first slip ring; 112. second slip ring; 113. third slip ring; 114. shell; 1141. button;

115. soft rubber channel; 1151. first bracket; 1152. circuit board; 1153. first housing;

1154. barbed member; 1155. metal contact; 1156. identification chip;

116. second bracket; 117. fixing ring; 118. third bracket; 1161. clamping strip; 1171. clamping groove; 1172. positioning strip; 1173. mounting hole; 1181. clamping column;

1157. first magnet; 1158. magnetic iron block; 1162. second magnet; 1111. third magnet;

119. soft rubber plug; 120. battery; 121. fixing rack; and 122. control mainboard.

DETAILED DESCRIPTION OF THE EMBODIMENTS

The present invention is further described below with reference to the accompanying drawings and embodiments. It may be understood that the specific embodiments described herein are used merely to explain the present invention, rather than to limit the present invention. It should be additionally noted that, for ease of description, only parts related to the present invention are shown in the drawings.

In the description of the present invention, unless otherwise expressly specified and limited, the terms “connected”, “connection”, and “fixed” should be understood in a broad sense. For example, it may be a fixed connection, a detachable connection, or integrated; it may be a mechanical connection or an electrical connection; and it may be directly connected, indirectly connected through an intermediate medium, internal communication between two components or an interactive relationship between two components. Those of ordinary skill in the art may understand the specific meanings of the above terms in the present invention according to the specific circumstances.

In the present invention, the state that the first feature is “over” or “under” the second feature may include a state that the first and second features are in direct contact with each other, or it may include a state that the first and second features are not in direct contact with each other and are in contact with each other via another feature between them, unless otherwise expressly specified and defined. Moreover, the state that the first feature is “over”, “above”, and “on” the second feature includes a state that the first feature is right above and obliquely above the second feature, or only indicates that the horizontal height of the first feature is greater than the horizontal height of the second feature. The state that the first feature is “under”, “below”, and “beneath” the second feature may include a state that the first feature is right below or obliquely below the second feature, or only indicates that the horizontal height of the first feature is less than the horizontal height of the second feature.

In the description of this embodiment, the orientations or positional relationships indicated by the terms “up”, “down”, “front”, “back”, “left”, “right”, etc. are based on the orientations or positional relationships shown in the accompanying drawings, only for the convenience of description and simplification of operation rather than indicating or implying that the apparatus or element referred to must have a particular orientation or be constructed and operated in a particular orientation, and therefore should not be construed as a limitation to the present invention. In addition, the terms “first” and “second” are used merely to distinguish the descriptions and do not have special meanings.

Figure 2:
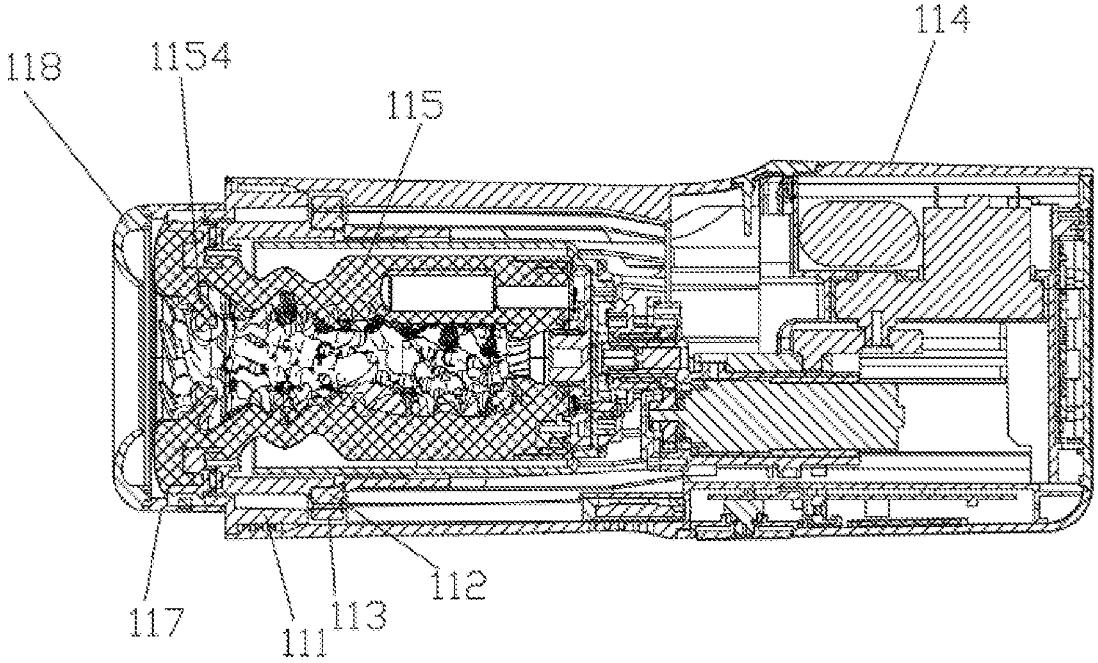
FIG. 2 is a sectional view of the present invention.
Figure 3:
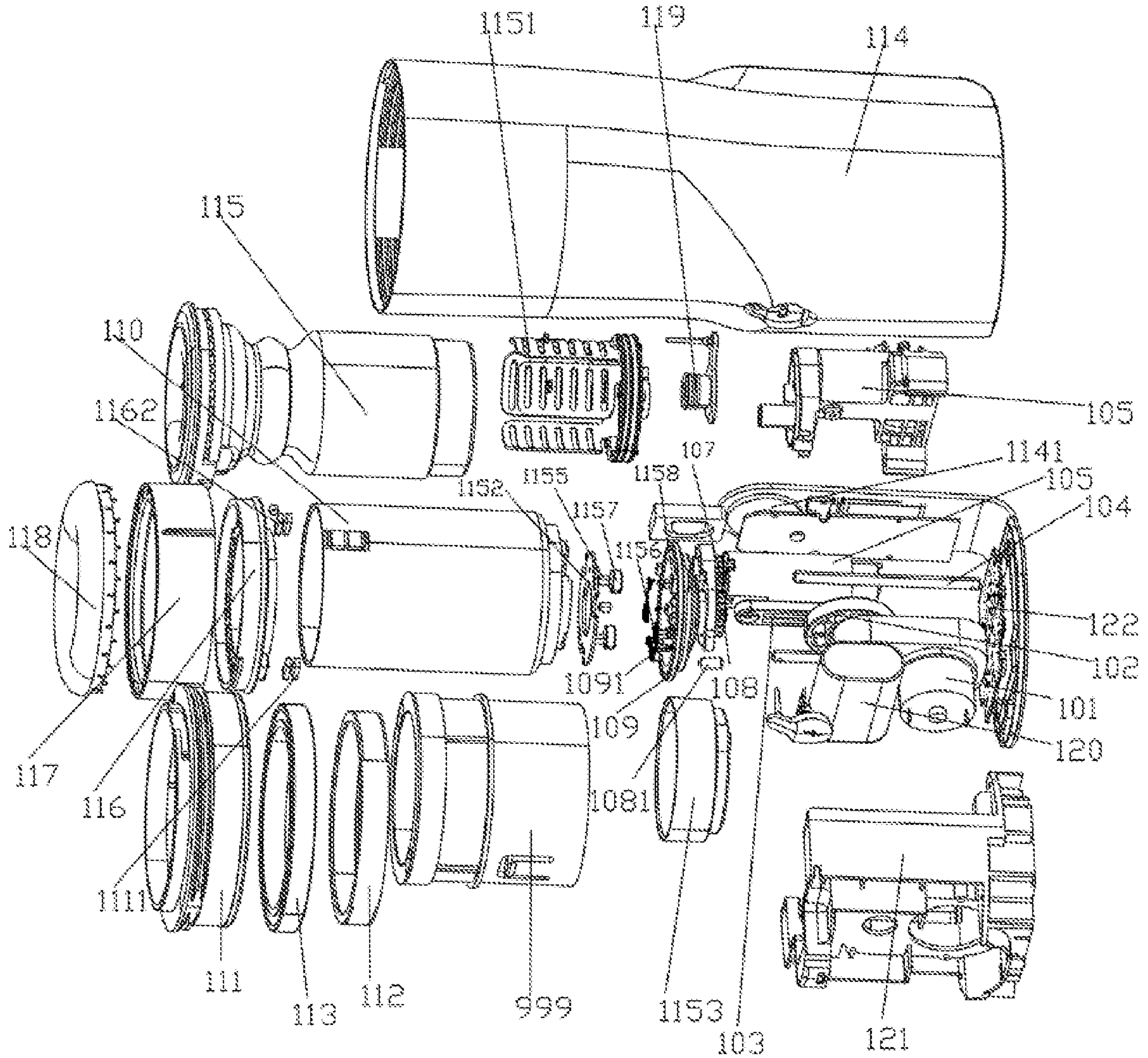
FIG. 3 is an exploded view of the present invention.
Figure 4:
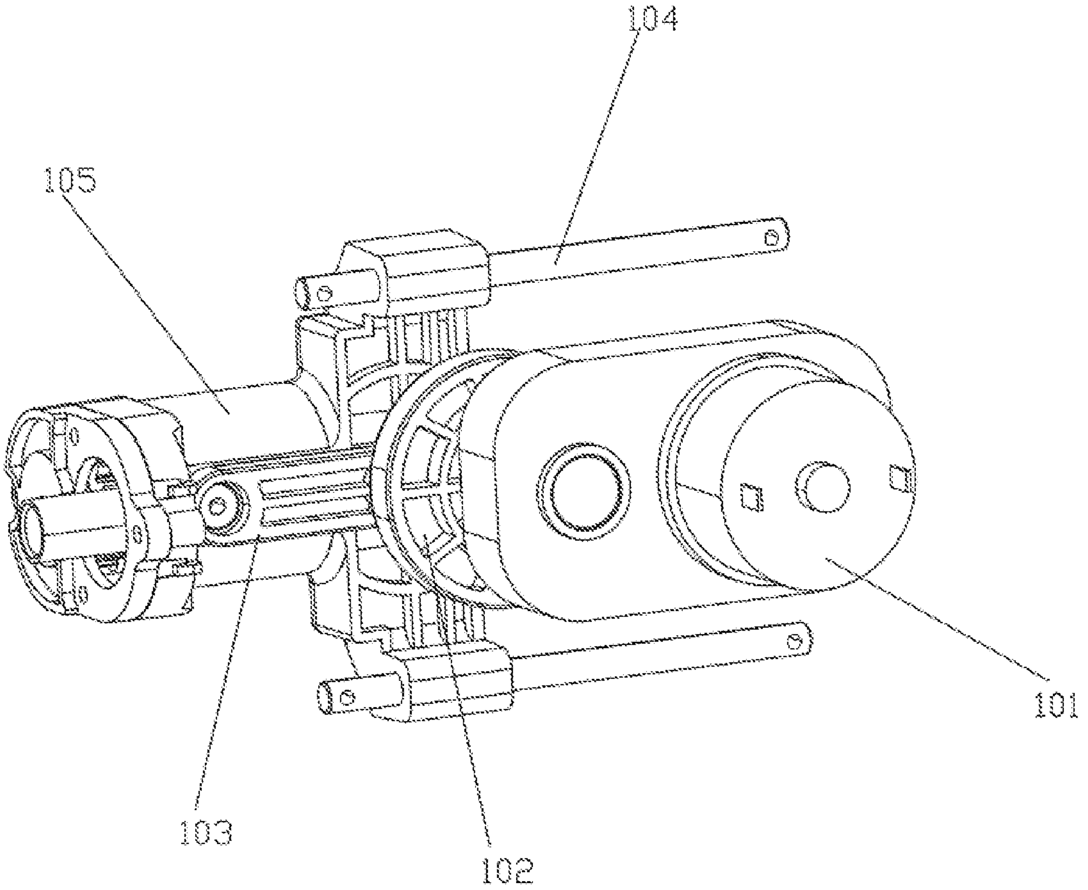
FIG. 4 is a three-dimensional view of a rotary mechanism and a telescopic mechanism in the present invention.
Figure 5:
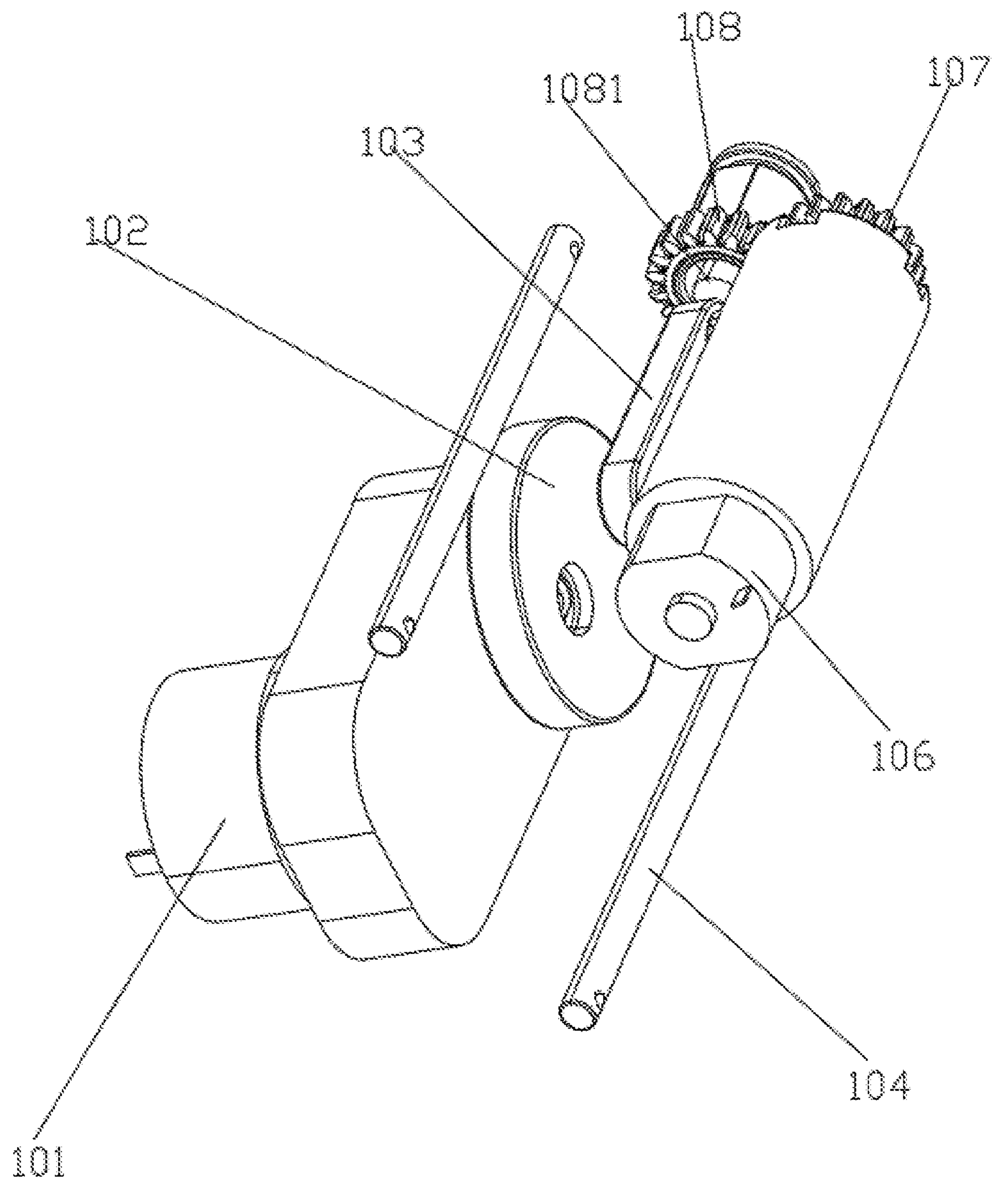
FIG. 5 is another three-dimensional view of a rotary mechanism and a telescopic mechanism in the present invention.
Figure 6:
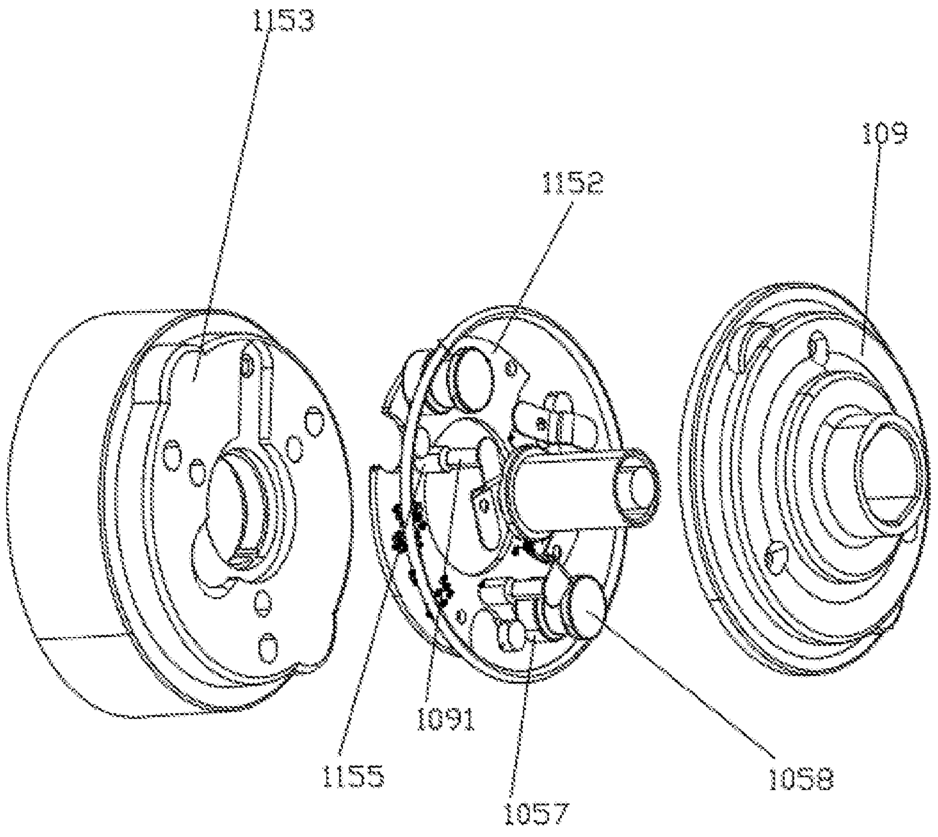
FIG. 6 is a three-dimensional view of a butt joint assembly and a disc plate in the present invention.
Figure 7:
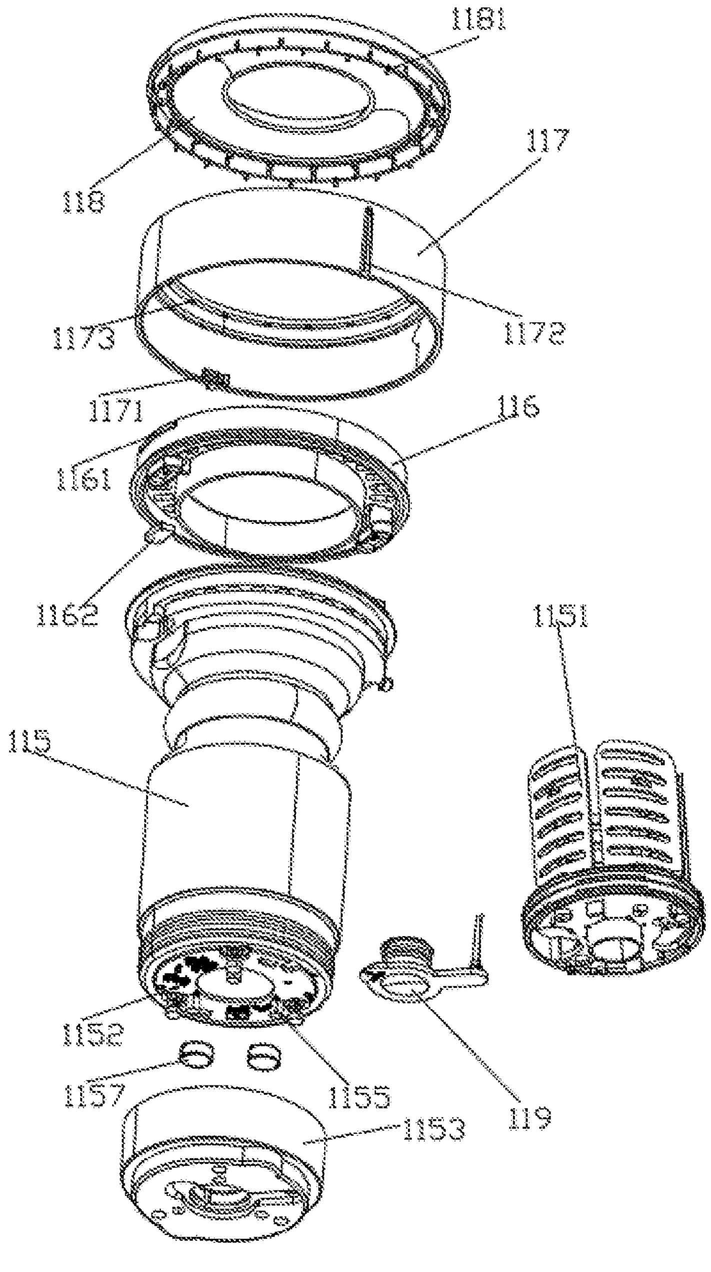
FIG. 7 is an exploded view of an inner container in the present invention.

As shown in FIG. 1 to FIG. 7, the present invention provides a novel rotary and telescopic sperm extractor, including: a telescopic mechanism: a rotary mechanism mounted on the telescopic mechanism; and an inner container mounted on the rotary mechanism, where the rotary mechanism rotates while making a reciprocating telescopic motion along with the telescopic mechanism, the telescopic mechanism includes a first motor 101, an eccentric wheel

102, and a rocker bar 103, the eccentric wheel 102 is mounted on the first motor 101, the rocker bar 103 has one end arranged on the eccentric wheel 102 and the other end mounted on the rotary mechanism, the first motor 101 drives the eccentric wheel 102 to rotate, the eccentric wheel 102 rotates to drive the rocker bar 103 to make a push-pull motion so as to implement the reciprocating telescopic motion of the rotary mechanism, and the inner container makes a reciprocating telescopic and rotary motion along with the rotary mechanism.

The telescopic mechanism further includes slide rods 104 and a slide block 105; a slide rod 104 is arranged on each of two sides of the slide block 105, one end, away from the first motor 101, of the rocker bar 103 is mounted on the slide block 105, the slide block 105 is pushed and pulled to make a reciprocating motion on the two slide rods 104, and the rotary mechanism is mounted on the slide block 105.

The rotary mechanism includes a second motor 106; the second motor 106 is mounted on the slide block 105 and rotates by a rotary shaft: a first gear 107 is further mounted on the rotary shaft of the second motor 106; the first gear 107 is further connected to a second gear 108 in a meshed manner; and a hollow structure is further arranged inside the second gear 108, and a rotary conductive slip ring 1081 is arranged in the hollow structure and configured to conduct electricity during rotation of the second gear 108.

A disc plate 109 is further arranged on the second gear 108 and rotates along with the second gear 108; three elastic metal columns 1091 are further mounted on the disc plate 109; a rotary barrel 110 is further mounted on the disc plate 109; a first slip ring 111 is further arranged on an outer side of a front end of the rotary barrel 110; and a second slip ring 112 is further arranged on a right side of the first slip ring 111 and further sleeved with a third slip ring 113, and the third slip ring 113 is mounted on a shell 114.

The inner container includes a soft rubber channel 115 located in the rotary barrel 110, and a butt joint assembly is further mounted at a tail end of the soft rubber channel 115; the butt joint assembly includes a first bracket 1151, a circuit board 1152, and a first housing 1153; the first bracket 1151 is embedded into the tail end of the soft rubber channel 115, the circuit board 1152 is mounted on the first bracket 1151, and the first housing 1153 is located on an outer side of the circuit board 1152 and mounted at the tail end of the soft rubber channel 115; and three metal contacts 1155 are arranged on the circuit board 1152 and extend to an outer side of the first housing 1153 to be in butt joint with the elastic metal columns 1091.

The circuit board 1152 is further provided with an identification chip 1156 configured to store identification information of the inner container so as to cause the sperm extractor to activate a corresponding mode.

The opening is further formed in the front end of the soft rubber channel 115, and the barbed member 1154 is further arranged at the opening and configured to prevent internal liquid from flowing out.

A second bracket 116 is further arranged at the front end of the soft rubber channel 115 and embedded into the soft rubber channel 115; a fixing ring 117 is further mounted on an outer side of the second bracket 116; a clamping strip 1161 is further arranged on an outer wall of the second bracket 116; a clamping groove 1171 is correspondingly formed in an inner wall of the fixing ring 117, and the clamping strip 1161 rotates and then is clamped into the clamping groove 1171 to fix the fixing ring 117 to the second bracket 116; a positioning strip 1172 is further arranged on an outer wall of the fixing ring 117; a third bracket 118 is further mounted on the fixing ring 117:

a plurality of clamping columns 1181 are further arranged on one side of the third bracket 118 that faces the fixing ring 117; and a plurality of mounting holes 1173 are correspondingly formed in the fixing ring 117, and the clamping columns 1181 are inserted into the mounting holes 1173 to fix the third bracket 118 to the fixing ring 117.

Two first magnets 1157 are further arranged in the first housing 1153, and magnetic iron blocks 1158 are further arranged at corresponding positions of the disc plate 109; a second magnet 1162 and a third magnet 1111 are further mounted on one side of the second bracket 116 and one side of the first slip ring 111 that are close to each other, respectively: and the first magnets 1157 and the magnetic iron blocks 1158 attract each other, and the second magnet 1162 and the third magnet 1111 attract each other for adsorptive positioning.

A soft rubber plug 119 is further arranged at the tail end of the soft rubber channel 115 through the circuit board 1152 and the first housing 1153 and configured to be taken down during cleaning so as to filter out remaining water inside:

a battery 120 is further arranged in the shell 114 and mounted on a fixing rack 121, and a button 1141 is further arranged on the shell 114; and a control mainboard 122 is further arranged on the fixing rack 121 and connected to the battery 120, the first motor 101, the second motor 106, the button 1141, and the circuit board 1152.

The principle of the present invention is as follows:

The rotary mechanism is mounted on the telescopic mechanism; the inner container is mounted on the rotary mechanism; the rotary mechanism rotates while making the reciprocating telescopic motion along with the telescopic mechanism; the telescopic mechanism includes the first motor 101, the eccentric wheel 102, and the rocker bar 103; the eccentric wheel 102 is mounted on the first motor 101, and the rocker bar 103 has one end arranged on the eccentric wheel 102 and the other end mounted on the rotary mechanism; and the first motor 101 drives the eccentric wheel 102 to rotate, the eccentric wheel 102 rotates to drive the rocker bar 103 to make the push-pull motion so as to implement the reciprocating telescopic motion of the rotary mechanism, and the inner container makes the reciprocating telescopic and rotary motion along with the rotary mechanism.

The three elastic metal columns 1091 are further mounted on the disc plate 109; the circuit board 1152 is mounted on the first bracket 1151, and the first housing 1153 is located on the outer side of the circuit board 1152 and mounted at the tail end of the soft rubber channel 115; the three metal contacts 1155 are arranged on the circuit board 1152 and extend to the outer side of the first housing 1153 to be in butt joint with the elastic metal columns 1091: and the circuit board 1152 is further provided with the identification chip 1156 configured to store the identification information of the inner container so as to cause the sperm extractor to activate the corresponding mode.

The two first magnets 1157 are further arranged in the first housing 1153, and the magnetic iron blocks 1158 are further arranged at the corresponding positions of the disc plate 109; the second magnet 1162 and the third magnet 1111 are further mounted on one side of the second bracket 116 and one side of the first slip ring 111 that are close to each other, respectively; and the first magnets 1157 and the magnetic iron blocks 1158 attract each other, and the second magnet 1162 and the third magnet 1111 attract each other for adsorptive positioning.

The soft rubber plug 119 is further arranged at the tail end of the soft rubber channel 115 through the circuit board 1152 and the first housing 1153 and configured to be taken down during cleaning so as to filter out remaining water inside.

The opening is further formed in the front end of the soft rubber channel 115, and the barbed member 1154 is further arranged at the opening and configured to prevent the internal liquid from flowing out.

The above are only the preferred embodiments of the present invention, rather than limiting the scope of patent of the present invention. Any equivalent structure transformations made using the content of the specification and the accompanying drawings of the present invention in an inventive conception of the present invention, directly or indirectly applied in other related technical fields, are all included within the scope of protection of the present invention.

What is claimed is:

1. A novel rotary and telescopic sperm extractor, comprising:

a telescopic mechanism;

a rotary mechanism mounted on the telescopic mechanism; and an inner container mounted on the rotary mechanism, wherein the rotary mechanism rotates while making a reciprocating telescopic motion along with the telescopic mechanism, the telescopic mechanism comprises a first motor, an eccentric wheel, and a rocker bar, the eccentric wheel is mounted on the first motor, the rocker bar has one end arranged on the eccentric wheel and the other end mounted on the rotary mechanism, the first motor drives the eccentric wheel to rotate, the eccentric wheel rotates to drive the rocker bar to make a push-pull motion so as to implement the reciprocating telescopic motion of the rotary mechanism, and the inner container makes a reciprocating telescopic and rotary motion along with the rotary mechanism;

wherein the telescopic mechanism further comprises slide rods and a slide block; and a slide rod is arranged on each of two sides of the slide block, one end, away from the first motor, of the rocker bar is mounted on the slide block, the slide block is pushed and pulled to make a reciprocating motion on the two slide rods, and the rotary mechanism is mounted on the slide block; and wherein the rotary mechanism comprises a second motor;

the second motor is mounted on the slide block and rotates by a rotary shaft;

a first gear is further mounted on the rotary shaft of the second motor; the first gear is further connected to a second gear in a meshed manner; and a hollow structure is further arranged inside the second gear, and a rotary conductive slip ring is arranged in the hollow structure and configured to conduct electricity during rotation of the second gear.

2. The novel rotary and telescopic sperm extractor according to claim 1, wherein a disc plate is further arranged on the second gear and rotates along with the second gear;

three elastic metal columns are further mounted on the disc plate;

a rotary barrel is further mounted on the disc plate;

a first slip ring is further arranged on an outer side of a front end of the rotary barrel; and a second slip ring is further arranged on a right side of the first slip ring and further sleeved with a third slip ring, and the third slip ring is mounted on a shell.

3. The novel rotary and telescopic sperm extractor according to claim 2, wherein the inner container comprises a soft rubber channel located in the rotary barrel, and a butt joint assembly is further mounted at a tail end of the soft rubber channel;

the butt joint assembly comprises a first bracket, a circuit board, and a first housing;

the first bracket is embedded into the tail end of the soft rubber channel, the circuit board is mounted on the first bracket, and the first housing is located on an outer side of the circuit board and mounted at the tail end of the soft rubber channel; and three metal contacts are arranged on the circuit board and extend to an outer side of the first housing to be in butt joint with the elastic metal columns.

4. The novel rotary and telescopic sperm extractor according to claim 3, wherein the circuit board is further provided with an identification chip configured to store identification information of the inner container so as to cause the sperm extractor to activate a corresponding mode.

5. The novel rotary and telescopic sperm extractor according to claim 3, wherein an opening is further formed in a front end of the soft rubber channel, and a barbed member is further arranged at the opening and configured to prevent internal liquid from flowing out.

6. The novel rotary and telescopic sperm extractor according to claim 3, wherein a second bracket is further arranged at the front end of the soft rubber channel and embedded into the soft rubber channel;

a fixing ring is further mounted on an outer side of the second bracket;

a clamping strip is further arranged on an outer wall of the second bracket; a clamping groove is correspondingly formed in an inner wall of the fixing ring, and the clamping strip rotates and then is clamped into the clamping groove to fix the fixing ring to the second bracket;

a positioning strip is further arranged on an outer wall of the fixing ring;

a third bracket is further mounted on the fixing ring;

a plurality of clamping columns are further arranged on one side of the third bracket that faces the fixing ring; and a plurality of mounting holes are correspondingly formed in the fixing ring, and the clamping columns are inserted into the mounting holes to fix the third bracket to the fixing ring.

7. The novel rotary and telescopic sperm extractor according to claim 6, wherein two first magnets are further arranged in the first housing, and magnetic iron blocks are further arranged at corresponding positions of the disc plate;

a second magnet and a third magnet are further mounted on one side of the second bracket and one side of the first slip ring that are close to each other, respectively; and the first magnets and the magnetic iron blocks attract each other, and the second magnet and the third magnet attract each other for adsorptive positioning.

8. The novel rotary and telescopic sperm extractor according to claim 7, wherein a soft rubber plug is further arranged at the tail end of the soft rubber channel through the circuit board and the first housing and configured to be taken down during cleaning so as to filter out remaining water inside;

a battery is further arranged in the shell and mounted on a fixing rack, and a button is further arranged on the shell; and a control mainboard is further arranged on the fixing rack and connected to the battery, the first motor, the second motor, the button, and the circuit board.

* * * * *